US010324610B2

(12) United States Patent
Lang

(10) Patent No.: US 10,324,610 B2
(45) Date of Patent: Jun. 18, 2019

(54) SELF SEDATION AND SUGGESTION SYSTEM

(71) Applicant: Hypnalgesics, LLC, Brookline, MA (US)

(72) Inventor: Elvira V. Lang, Brookline, MA (US)

(73) Assignee: Hypnalgesics, LLC, Brookline, MA (US)

( * ) Notice: Subject to any disclaimer, the term of this patent is extended or adjusted under 35 U.S.C. 154(b) by 169 days.

(21) Appl. No.: 15/341,958

(22) Filed: Nov. 2, 2016

(65) Prior Publication Data

US 2017/0060403 A1 Mar. 2, 2017

Related U.S. Application Data

(63) Continuation of application No. 14/488,143, filed on Sep. 16, 2014, now Pat. No. 9,495,126.

(60) Provisional application No. 61/946,194, filed on Feb. 28, 2014.

(51) Int. Cl.
| | |
|---|---|
| *G06F 3/16* | (2006.01) |
| *G06F 19/00* | (2018.01) |
| *G10L 13/00* | (2006.01) |
| *G16H 10/20* | (2018.01) |
| *G06F 3/0482* | (2013.01) |
| *G06F 3/0484* | (2013.01) |
| *G11B 27/036* | (2006.01) |

(52) U.S. Cl.
CPC ........ *G06F 3/04847* (2013.01); *G06F 3/0482* (2013.01); *G06F 3/165* (2013.01); *G06F 19/3481* (2013.01); *G11B 27/036* (2013.01); *G16H 10/20* (2018.01); *G10L 13/00* (2013.01)

(58) Field of Classification Search
CPC .......... G06F 17/3074; G06F 17/30772; G06F 17/30029; G06F 17/30056
See application file for complete search history.

(56) References Cited

U.S. PATENT DOCUMENTS

| | | |
|---|---|---|
| 5,337,258 A | 8/1994 | Dennis |
| 5,377,258 A | 12/1994 | Bro |
| 5,456,606 A | 10/1995 | McIntyre et al. |
| 5,555,536 A | 9/1996 | Rolf et al. |
| 5,596,994 A | 1/1997 | Bro |
| 5,877,445 A | 3/1999 | Hufford et al. |

(Continued)

OTHER PUBLICATIONS

Hypnosis Scripts Creator, "Sussex Therapy Centre: Hypnotherapy, Coaching, Training & Research in West Sussex," http://www.sussexhypnotherapycentre.co.uk/hypnosisscriptscreator.com, Jan. 31, 2014, pp. 1-6.

(Continued)

*Primary Examiner* — Matthew H Baker
(74) *Attorney, Agent, or Firm* — Neal, Gerber & Eisenberg LLP

(57) ABSTRACT

A computerized system and method for modifying a pre-existing hypnotic script into a custom-made script for use in self-sedation by a user is disclosed. In one sense, the system can collect an input from a user specifying a desired time length and automatically adjust the playback length to accommodate the user by snippet selection and replacement from a collection of snippets stored in a memory. Snippet selection may be based on a variety of factors, which include a user's particular style preferences determined through an indirect analysis.

17 Claims, 13 Drawing Sheets

(56) References Cited

U.S. PATENT DOCUMENTS

| | | |
|---|---|---|
| 6,032,156 A | 2/2000 | Marcus |
| 6,051,770 A | 4/2000 | Milburn et al. |
| 6,057,846 A | 5/2000 | Sever et al. |
| 6,199,076 B1 | 3/2001 | Logan et al. |
| 6,296,489 B1 | 10/2001 | Blass et al. |
| 6,565,504 B2 | 5/2003 | Blumenthal |
| 6,605,770 B2 | 8/2003 | Yamane et al. |
| 6,760,696 B1 | 7/2004 | Goldberg et al. |
| 6,938,209 B2 | 8/2005 | Ogawa et al. |
| 7,394,011 B2 | 7/2008 | Huffman |
| 7,670,263 B2 | 3/2010 | Ellis et al. |
| 7,754,959 B2 | 7/2010 | Herberger et al. |
| 7,827,039 B2 | 11/2010 | Butcher et al. |
| 7,863,511 B2 | 1/2011 | McNally |
| 7,977,560 B2 | 7/2011 | Marcus |
| 8,022,287 B2 | 9/2011 | Yamashita et al. |
| 8,058,544 B2 | 11/2011 | Hoeberechts et al. |
| 8,161,039 B2 | 4/2012 | Nielen et al. |
| 8,517,912 B2 | 8/2013 | Clare |
| 8,649,891 B2 | 2/2014 | Glatt et al. |
| 8,727,981 B2 | 5/2014 | Bechtel et al. |
| 8,874,538 B2 | 10/2014 | Mate et al. |
| 8,956,290 B2 | 2/2015 | Gilley et al. |
| 9,037,578 B2 | 5/2015 | Brust et al. |
| 9,110,958 B2 | 8/2015 | Brust et al. |
| 9,213,705 B1 | 12/2015 | Story, Jr. et al. |
| 9,251,713 B1 | 2/2016 | Giovanniello et al. |
| 2001/0005770 A1 | 6/2001 | Blumenthal |
| 2003/0046090 A1 | 3/2003 | Brown |
| 2004/0267565 A1 | 12/2004 | Grube |
| 2005/0060642 A1 | 3/2005 | Duncombe |
| 2006/0161850 A1 | 7/2006 | Seaberg |
| 2007/0014537 A1 | 1/2007 | Wesemann et al. |
| 2007/0074619 A1 | 4/2007 | Vergo |
| 2007/0106750 A1 | 5/2007 | Moore |
| 2009/0055214 A1 | 2/2009 | Butcher et al. |
| 2009/0281392 A1 | 11/2009 | Brown |
| 2010/0217111 A1 | 8/2010 | Dietz |
| 2010/0231483 A1 | 9/2010 | Bazih et al. |
| 2010/0293463 A1 | 11/2010 | Snyder et al. |
| 2011/0161348 A1 | 6/2011 | Oron |
| 2011/0283190 A1 | 11/2011 | Poltorak |
| 2012/0035925 A1 | 2/2012 | Friend et al. |
| 2012/0157758 A1 | 6/2012 | Dietz |
| 2013/0225950 A1 | 8/2013 | Van Elswijk et al. |
| 2013/0236865 A1 | 9/2013 | Hamui |
| 2013/0245364 A1 | 9/2013 | Gillies et al. |
| 2014/0280156 A1 | 9/2014 | Maser et al. |
| 2015/0082170 A1 | 3/2015 | Mitchell |
| 2017/0039045 A1* | 2/2017 | Abrahami .............. G06F 8/65 |

OTHER PUBLICATIONS

SHARM 4 User Guide, 2012, pp. 1-73.

Delroy Cameron et al., "Predose: A semantic web platform for drug abuse epidemiology using social media", Journal of Biomedical Informatics, Dec. 31, 2013, vol. 46, Issue 6, pp. 985-997. See abstract and pp. 991-994.

International Search Report and Written Opinion for International Patent Application No. PCT/US2015/017546 dated May 28, 2015.

International Preliminary Report on Patentability for International Patent Application No. PCT/US2015/017546 dated Nov. 4, 2015. (29 pages).

* cited by examiner

Style Analysis — 170

On a scale of 1 to 5, please indicate your agreement with the following statements.

- I find other people fascinating.
- My voice uses a broad pitch spectrum.
- I prefer that others start the conversation.
- I tend to speak quickly.

SELF SEDATION AND SUGGESTION SYSTEM

CROSS-REFERENCE TO RELATED APPLICATION

This application claims the benefit of U.S. Provisional Patent Application No. 61/946,194, filed on Feb. 28, 2014, and is a continuation of U.S. Non-Provisional Patent application Ser. No. 14/488,143, filed on Sep. 16, 2014, the contents of which are fully incorporated herein by reference.

TECHNICAL FIELD

This invention relates generally to the field of hypnosis and psycho-physiological conditioning, and more specifically, to systems and methods for enabling patients or clients to create and utilize customized hypnotic or otherwise suggestive electronic media for playback, such as through a computerized application.

BACKGROUND OF THE INVENTION

Hypnosis and related forms of non-pharmaceutical sedation are well known and frequently implemented tools used to assist people in achieving a variety of objectives, such as, for example, to reduce fear or anxiety, to increase focus on a specific task, to curb an undesirable behavior, or to help control other emotions. In a traditional scenario, a therapist will work with a patient in a one on one setting to help the patient focus in order to access the patient's subconscious and provide suggestions relating to achievement of a desired goal. Ideally, the patient is able to access the benefits of the therapy once the therapy session is over, and at the time(s) when the goal is to be achieved. For example, a first patient might need help fighting the urge to have a cigarette. During therapy, suggestions are implanted that cause the patient to relate the taste of cigarettes with something bad, such that the later thought of them is less appealing. In another example, a second patient may experience high anxiety each time they visit the dentist. During therapy, suggestions are implanted to help associate the waiting room of the dentist's office with a sense of calm. However, people that seek hypnotic or related non-pharmaceutical sedation treatments (referred to herein in a non-limiting manner as "patients") often cannot access the suggestions at the proper time, or the anxieties or impulses relating to the goal may overcome the strength of the suggestion. In these cases, patients can benefit from a more timely delivery of the suggestion, so that it is received at the time when most needed.

It has been recognized that therapy sessions may be pre-recorded and played back on demand. For example, U.S. Publ. No. 2013/0236865 entitled "Systems and Methods for Modifying Human Behavior Using an Audio Recording During Sleep" teaches the playback of a recorded therapy session during sleep to help reinforce the therapeutic message. However, the session is generated manually by the therapist, and cannot be modified or tailored for a specific need by the patient upon demand. U.S. Pat. No. 6,057,846 entitled "Virtual Reality Psychophysiological Conditioning Medium teaches a "virtual reality device" used to induce a state of meditation or hypnosis upon demand. But the message is still pre-determined by the therapist and not adjustable by the user. Such messages may not fit the immediate need of the patient, or may not fit the time window that the patient has available.

Somewhat more flexibility and user control is suggested by U.S. Pat. No. 6,565,504 entitled "Method and Apparatus to Create and Induce a Self-Created Hypnosis," which teaches an "interactive computer device" that presents a "custom hypnosis script" to induce hypnosis and make behavioral suggestions. According to the invention, a user submits responses to pre-set questions that form gaps in an already existing or pre-assembled script, e.g., "pre-programmed textual material." A script is assembled based on these inputs and sent back to the user. While this adds slightly more flexibility, the user is still stuck with the formal nature of the pre-set questions, and it is really the therapist that is creating the script using the responses. The length of the script or audio file is pre-established by the therapist or the program written at the request of the therapist. Patients (users) must be careful not to induce a state of hypnosis during which they will be needed to perform complex activities. If the script lasts 30 minutes, the patient must have at least that much time to dedicate to listening to the script in the prior art systems. However, a patient in a dental waiting room, for example, may have only a few minutes before their scheduled appointment. They need a quick, tailored solution available to help ease their anxiety.

What is needed is a software solution that provides superior flexibility to the user of the hypnosis script, and provides them a solution that does not rely on the input or control of a therapist in situations where that is not practical or possible. The patient should be able to establish the length of the script, and it can be assembled (dynamically, if necessary) to accommodate that time window. Furthermore, options and selections are needed that can allow a user to fully tailor the script to their purpose, rather than simply providing answers to pre-set questions. An improved solution would involve truly tailored inputs, e.g., where the user can provide material that can be placed within the script for compilation with other content that is then automatically assembled into a customized script for playback.

SUMMARY OF THE INVENTION

The present invention comprises a system and method for automatically compiling a personalized media file that can be used to assist in goal achievement through non-pharmaceutical sedation. According to a particular embodiment, the invention comprises a computer application that presents a user interface for allowing a user to interface with the program and set up a personally tailored script. The application may provide for audio recording, such as of the user's voice, for purposes of receiving a tailored message to be synchronized with pre-recorded material. The patient may proscribe a time window or specific time length that the script to be generated should last. Based on these and possibly other inputs, the application generates a truly tailored, suggestive script for playback by the patient at the patient's discretion. The script may then be electrically stored in a data memory for later use.

In another embodiment, the invention comprises a computer application that presents a user interface for allowing a user to interface with the program and set up a personally tailored script. The application may provide for submission of a sound bite captured in, for example, a .AVI file or other sort of sound file, such as a snippet of a song, a verbal message spoken in a particular tone of voice, etc. The term "snippet" is used within this disclosure to generally refer to any digitally-captured short audio sound bite, whether it be music (a music snippet), spoken word (e.g., a message snippet), any other auditory sound, or even recorded silence.

As used herein, a snippet may be many seconds or even a minute long, but is often only a few seconds or even a fraction of a second in playback length (play time). Snippets are used to create a tailored message to be synchronized in order to form a script. A snippet may be voice, music, or even a video component. It may be pre-recorded and stored in a database for use by the system, or it may be user-provided. A user snippet could be a recording of the user's voice providing a message component such as a reminder, text provided by the user and converted into a snippet by the system, or some pre-existing media file clip provided by the user and not within the system collection.

As used herein, the term "script" is a complete electronic media file (typically an audio file, but it may have a video component) that will be several minutes long, and is the output of the system. The patient may proscribe a time window or specific time length that the script to be generated should last. Based on these and possibly other inputs, the application generates a truly tailored suggestive script for playback by the patient at the patient's discretion. The script may then be stored in a memory for later use.

In still another embodiment, the invention comprises a computer application that presents a user interface for allowing a user to interface with the application to set up a self-designed script. The application solicits input from the patient by asking indirect questions about the patient's interests, goals, and other characteristics. Instead of placing direct feedback from the patient into the script, the application uses responses to the indirect questions and interprets those responses using pre-programmed analytical guidelines to select specific pre-programmed content based on the user responses. In this manner, the application automatically selects the content such that it will be best suited for (and delivered in the most suitable manner to) the patient. The content is then used to generate a truly tailored suggestive script for playback by the patient at the patient's discretion. The script may then be electronically stored in a data memory for later use.

In some variations of the above-described embodiments or other embodiments, the computer application may be able to dynamically adjust the length of a pre-recorded personally tailored script. For example, if the patient originally requested that the script be 8 minutes long, but now knows that they have only 4 minutes before an event is to take place, the user could request that the application trim components of the script such that it completes in 4 minutes. In this manner, the patient is not in a compromised mental state at the time when the event is to occur, but rather is alert and fortified with the script's message.

Thus, the invention provides a new and useful system and method for automatically assembling a tailored hypnotic or therapeutic message for use by patients at the time of (or just prior to) facing a challenge or attempting to achieve a goal. While certain embodiments are referenced above, other embodiments, systems, methods, features, and advantages of the present invention will be, or will become, apparent to one having ordinary skill in the art upon examination of the following figures and detailed description. In some cases, embodiments may incorporate one or more of the features from the above-referenced embodiments. It is intended that all such additional systems, methods, features, and advantages included within this description, be within the scope of the present invention, and be protected by the accompanying claims.

BRIEF DESCRIPTION OF THE DRAWINGS

The present invention can be better understood with reference to the following figures.

FIG. 7 depicts a screen for gathering input for use in selection and delivery of indirect suggestions, according to certain embodiments of the self sedation and suggestion system application.

DETAILED DESCRIPTION

Figure 1:
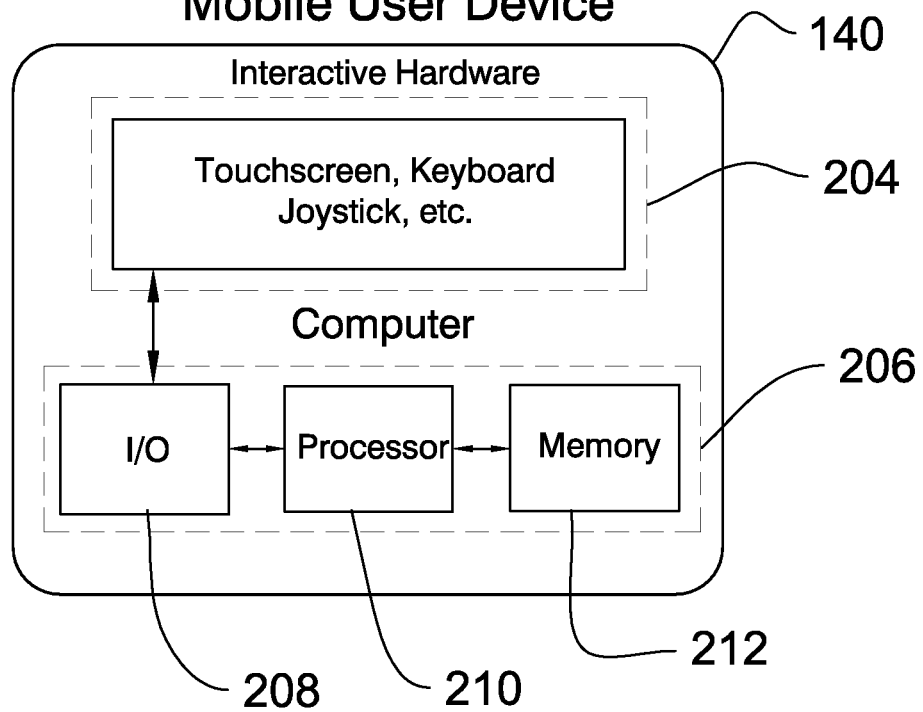
FIG. 1 depicts aspects of a mobile device serving as a general purpose computer for facilitating aspects of the invention.

The description that follows describes, illustrates and exemplifies one or more particular embodiments of the present invention in accordance with its principles. This description is not provided to limit the invention to the embodiments described herein, but rather to explain and teach the principles of the invention in such a way as to enable one of ordinary skill in the art to understand these principles and, with that understanding, be able to apply to practice not only the embodiments described herein, but also other embodiments that may come to mind in accordance with these principles. The scope of the present invention is intended to cover all such embodiments that may fall within the scope of the appended claims, either literally or under the doctrine of equivalents.

It should be noted that in the description and drawings, like or substantially similar elements or steps may be labeled with the same reference numerals. However, sometimes these elements or steps may be labeled with differing numbers, such as, for example, in cases where such labeling facilitates a more clear description. Such labeling and drawing practices do not necessarily implicate an underlying substantive purpose. As stated above, the present specification is intended to be taken as a whole and interpreted in accordance with the principles of the present invention as taught herein and understood to one of ordinary skill in the art.

The present invention relates to a software application, and its associated functionality. While the invention will always require a user interface of some sort (e.g., inputs and outputs), and access to a memory and processor to operate the application and underlying system, the invention can be practiced using different hardware scenarios. For example, the application could be stored in a memory at a remote server or otherwise operate through the "cloud" in a distributed network system. In this case, the user would merely have the interface which would receive all commands and executions from a remote processor. In other scenarios, the application and all associated data in memory could be stored on a single hardware device in the possession of the user. In still other scenarios, a user could have a device, such as a mobile smartphone, that comprises the user interface, a memory, and a processor, but is in contact with a remote server that has access to additional data stored in a central memory.

Though the application described herein can operate in any such hardware configuration, it is explained herein as used in association with a mobile device (such as a smart phone or tablet) so that a user can access the software wherever needed. Though the invention is explained using mobile user device 140 as an exemplary device, it will be understood that use of the system need not be on such a device and the specific type of user device used does not limit the scope of the claimed invention. For example, the mobile device could be a smart watch, GOOGLE GLASSES, or some other such wearable device.

Referring to FIG. 1, a schematic diagram of certain aspects of a mobile device 140 is provided. This exemplary mobile device 140 includes an interactive hardware portion 204 and a computer portion 206. The interactive hardware portion 204 can include one or more of a touch screen, a keyboard, a stylus, a joystick, a microphone and the like, which can be arranged in various manners and have different shapes without changing the spirit of the interaction of the hardware portion 204 with the computer portion 206. The touch screen can be a liquid display crystal (LCD), display screen, a plasma screen, a light emitting diode (LED), or any other screen capable of displaying text and images.

The computer portion 206 includes an input/output (I/O) portion 208, a central processing unit (CPU) portion 210 (i.e., a microprocessor), and a memory 212. The CPU portion 210 can be any computer-processing unit from a singular microchip to extensive microchip configurations. The memory portion 212 can include, without limitation, any one or a combination of volatile memory elements (e.g., random access memory (RAM, such as DRAM, SRAM, SDRAM, etc.)) and nonvolatile memory elements (e.g., ROM, hard drive, tape, CDROM, etc.). Moreover, the memory portion 212 may incorporate electronic, magnetic, optical, and/or other types of storage media, and can have a distributed architecture where various components are situated remote from one another, but are still accessed by CPU portion 210. The interactive hardware portion 204 is coupled to the I/O portion 208 such that a command entered by a user or customer through the interactive hardware portion 204 will be forwarded to the I/O portion 208, to the processor portion 210 and then to memory portion 212. The input/output portion 208 may provide, for example, a keyboard for text input, a digital recording device for capturing music or voice input, cursors, touch screens, etc. It may also include speakers, audio ports, LCD screens, etc., for output to the user.

Figure 2:
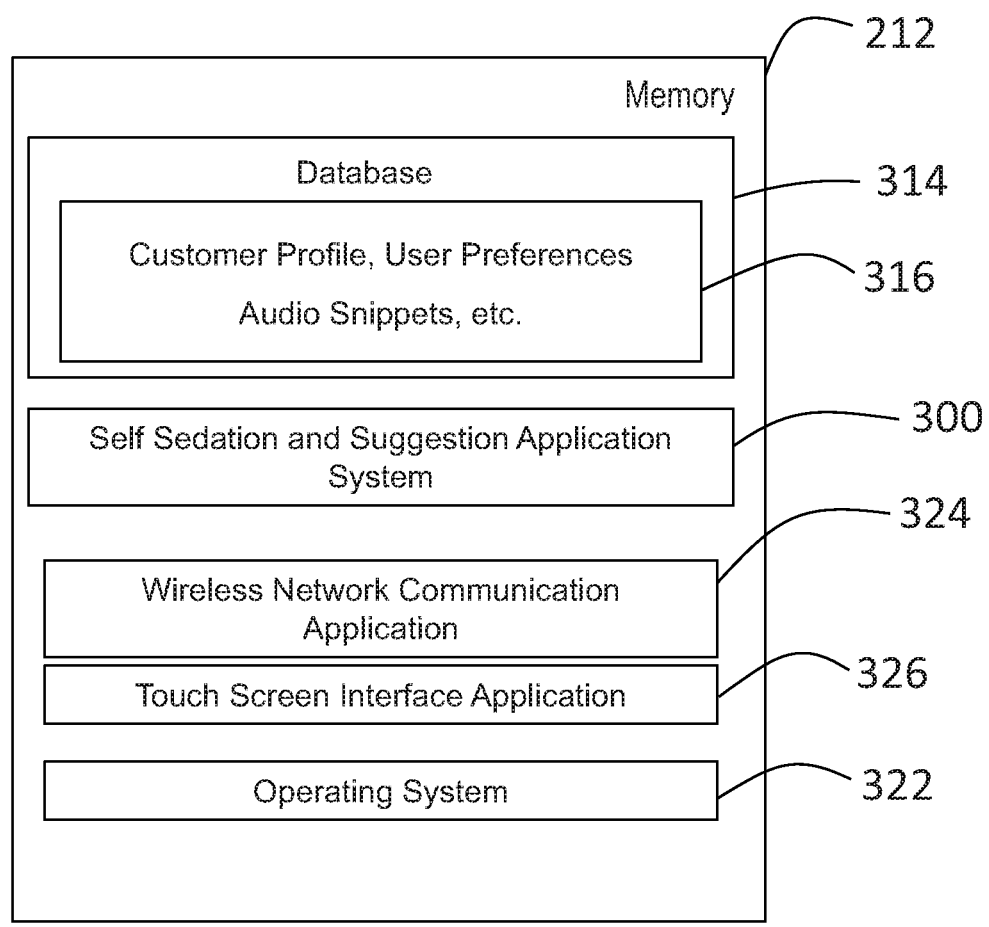
FIG. 2 depicts contents of a memory component of the mobile device of FIG. 1.

As illustrated in FIG. 2, a schematic diagram of the memory portion 212 of FIG. 1 is shown. The memory portion 212 can include or store a database 314, executable programs 300, 326, and 324, and an operating system 322. The database 314 can store data related to prior use of the self sedation and suggestion system application 300 by a user, such as, for example, the user's username, password, preferences, saved scripts, or other data as discussed below. The executable programs include the self sedation and suggestion system application 300, a touch screen interface application 326, and a wireless network communication software application 324 such as a common browser like Internet Explorer. Various other executable programs may also be stored in memory 212 that are unrelated to the present invention. Verification data reader application 320 may be a sub-code segment or part of the OMS application component 318, or may be a separate, callable application residing independently in memory 212.

When the mobile device 140 is in operation, the processor 210 is configured to execute software stored within the memory 212 to communicate data to and from memory 212 and to generally control operations of mobile device 140 pursuant to the software. The self sedation and suggestion system application 300 and the operating system 322, in whole or in part but typically the latter, are read by the processor 210, perhaps buffered within the processor 210, and then executed. When the hypnosis application 300 is implemented in software, it can be stored on any computer readable medium for use by or in connection with any computer related system or method. The self sedation and suggestion system application 300 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In the context of this document, a "computer-readable medium" can be any means that can store, communicate, propagate, or transport the program for use by or in connection with the instruction execution system, apparatus, or device. The computer readable medium can be for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). In another embodiment, where the self sedation and suggestion system application 300 is implemented in hardware, it can be implemented with any, or a combination of, the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Before proceeding to a discussion of the function of the self sedation and suggestion system application 300, it will be understood that the application is designed to function as a stand-alone application that does not require external network access to operate. Initially, the application 300 must be loaded onto the mobile device 140, such as, for example, by downloading the application 300 from a network. However, once downloaded, the application can be launched and can function without remotely-accessed information. However, it will also be understood that users may access additional content, such as pre-recorded reminders, images (still pictures or scrolling video), background music, or full scripts, as will be further discussed below, by connecting to the cloud or to a remote server where such additional content may be acquired for use with the application 300.

Figure 3:
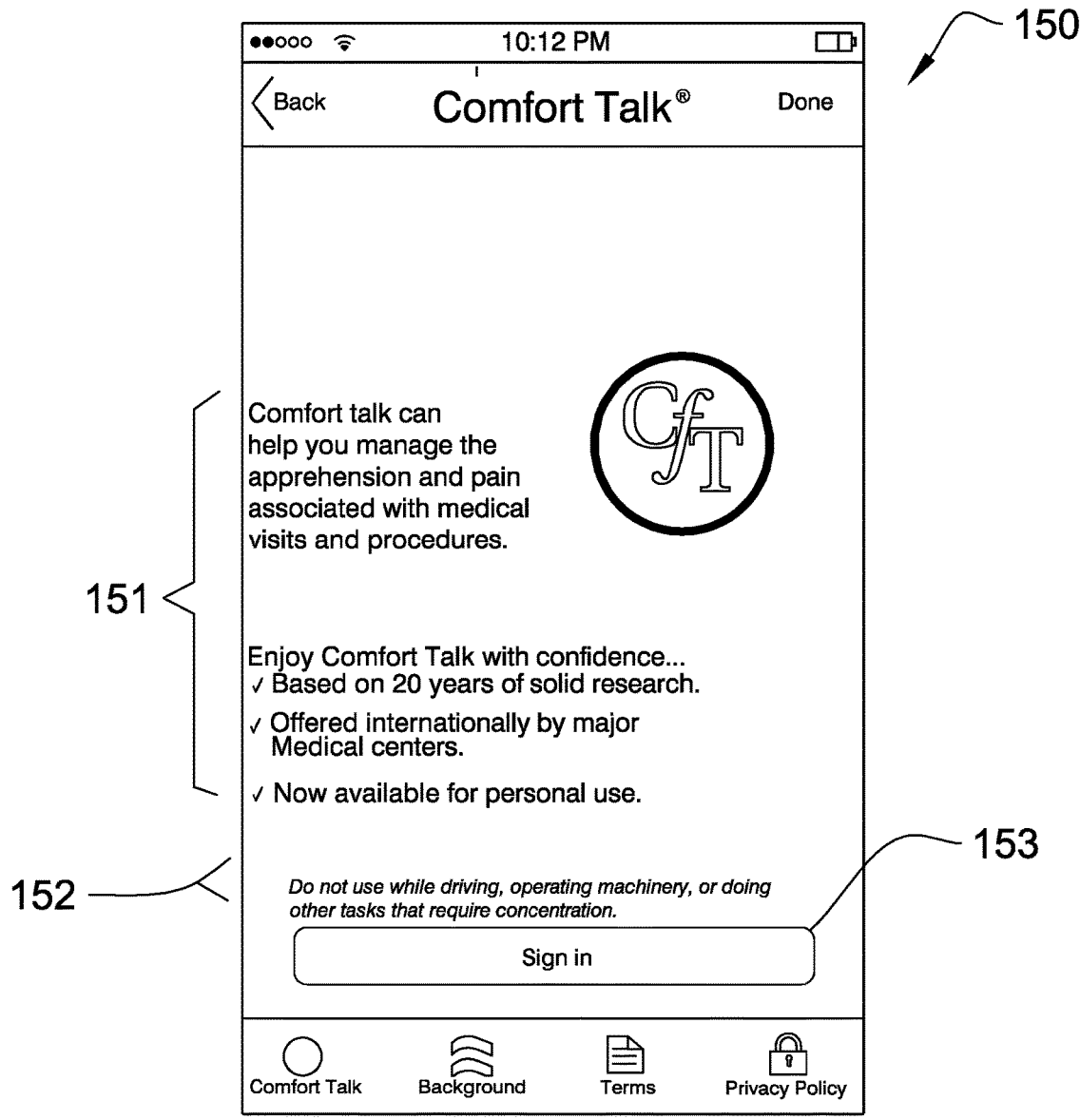
FIG. 3 depicts an exemplary graphical user interface of a self sedation and suggestion system application, according to certain embodiments.

Turning to FIG. 3, a user of the mobile device 140 has elected to launch self sedation and suggestion system application 300 and has arrived at a welcome screen 150. It will be understood that the display screens of the illustrated embodiment are non-limiting in their screen design, layout, or naming of particular options or selections. Rather, it is the functionality of the application and interaction with the user through the interface screens that defines the invention. The welcome screen may offer information or advertising such as advertising text 151, instructions, disclaimers or warnings such as instructional text 152, and a start or sign in execution such as sign in button 153. Though a sign-in feature is not necessary in all embodiments, it allows the application 300 to access material specific to the user (whether present in memory 212 on device 140 or remotely via network communication from a remote server). This material is then used by the application to call upon information saved from past sessions with the user, as described below. In the illustrated embodiment, if a user has never used application 300, they will not have a password and will be prompted for startup account information.

Figure 4:
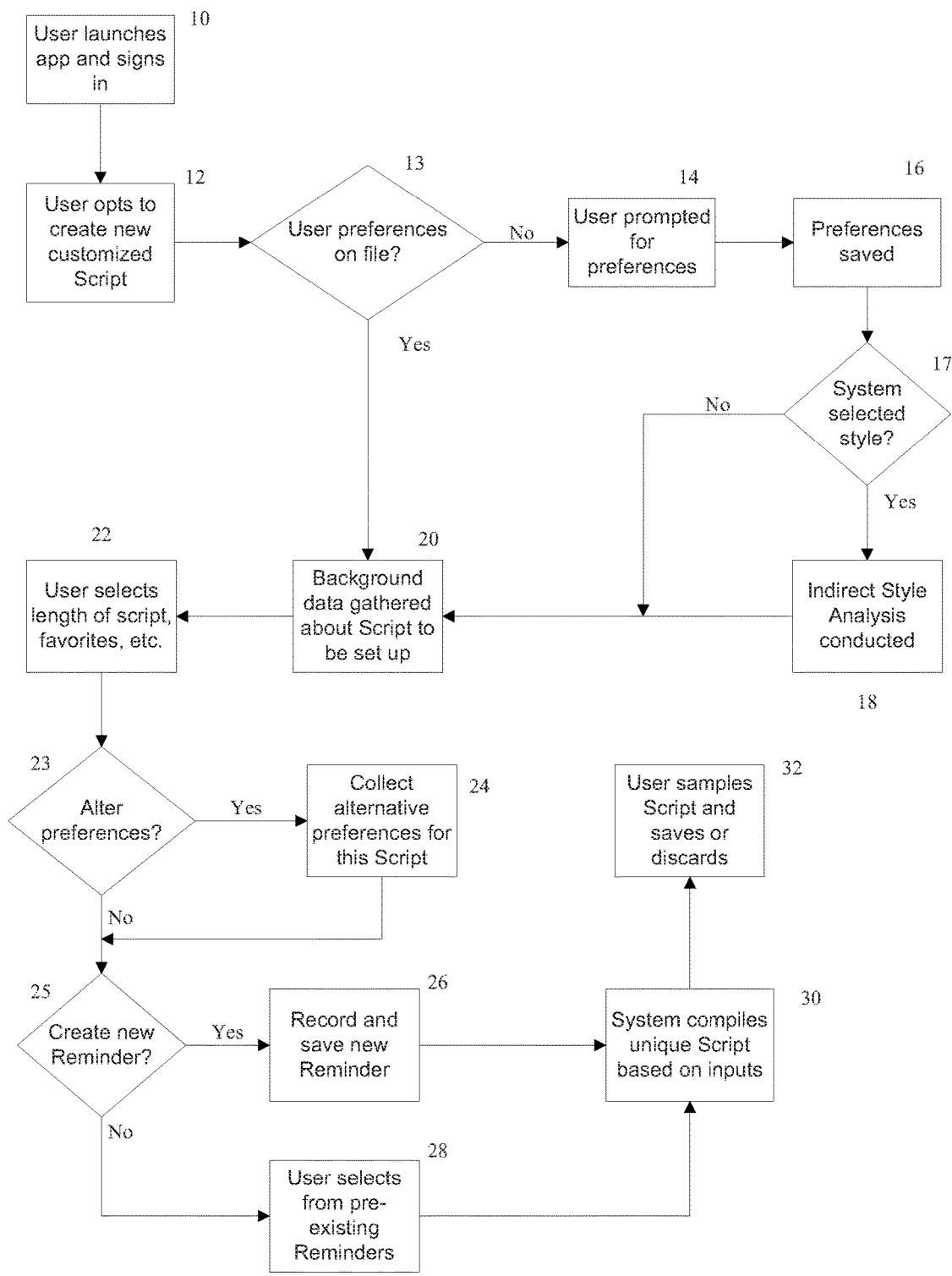
FIG. 4 is a flow chart showing process steps of the self sedation and suggestion system application of FIG. 3, according to certain embodiments.
Figure 5:
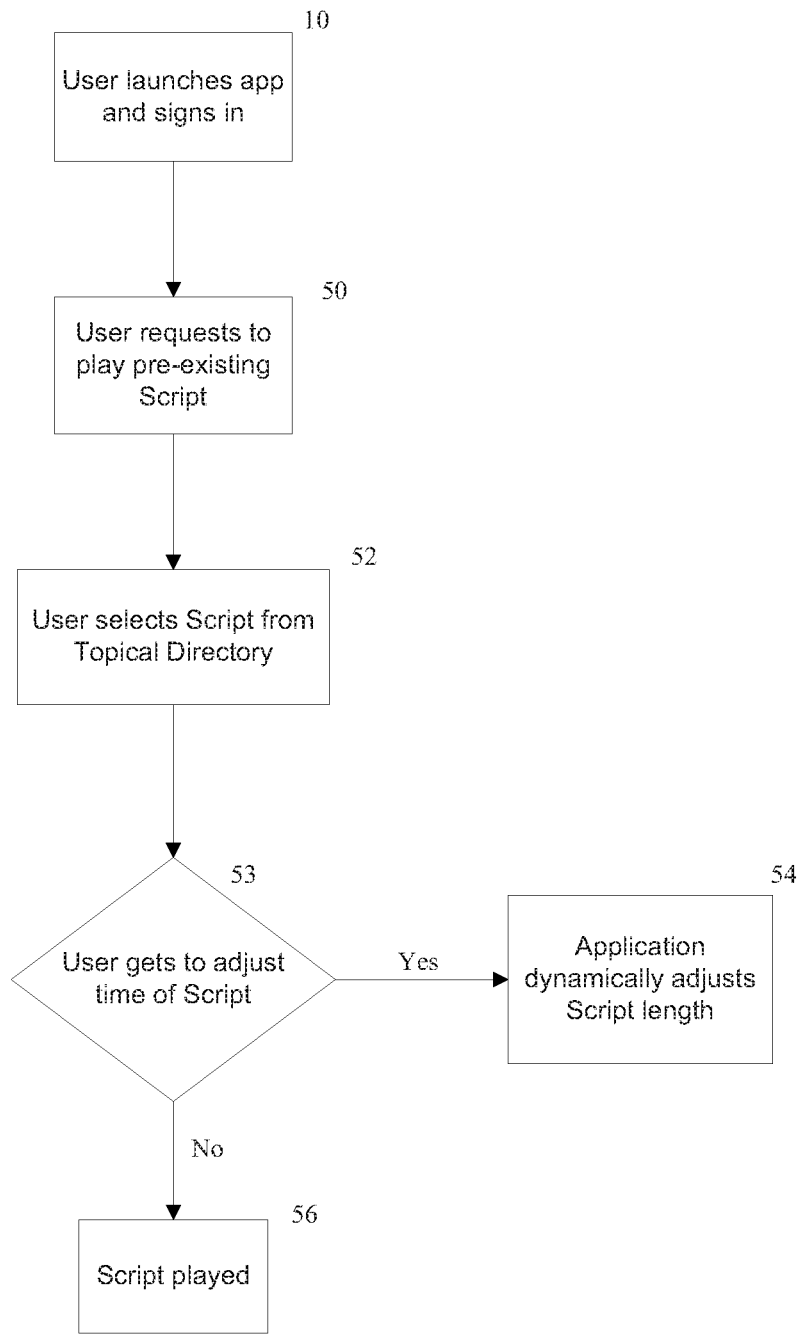
FIG. 5 is a flow chart showing other process steps of the self sedation and suggestion system application of FIG. 3, according to certain embodiments.

FIGS. 4 and 5 illustrate exemplary flow charts that walk through certain functional steps of operation of application 300. Both figures start at step 10 from the sign-in screen (such as that of FIG. 3). FIG. 4 focuses on a scenario where a user opts to create a new script, while FIG. 5 focuses on a scenario where a user selects from a pre-existing or pre-assembled script. Exemplary screen shots showing interfaces that a user might experience as they step through the application will be discussed concurrently with the flow charts.

Figure 6:
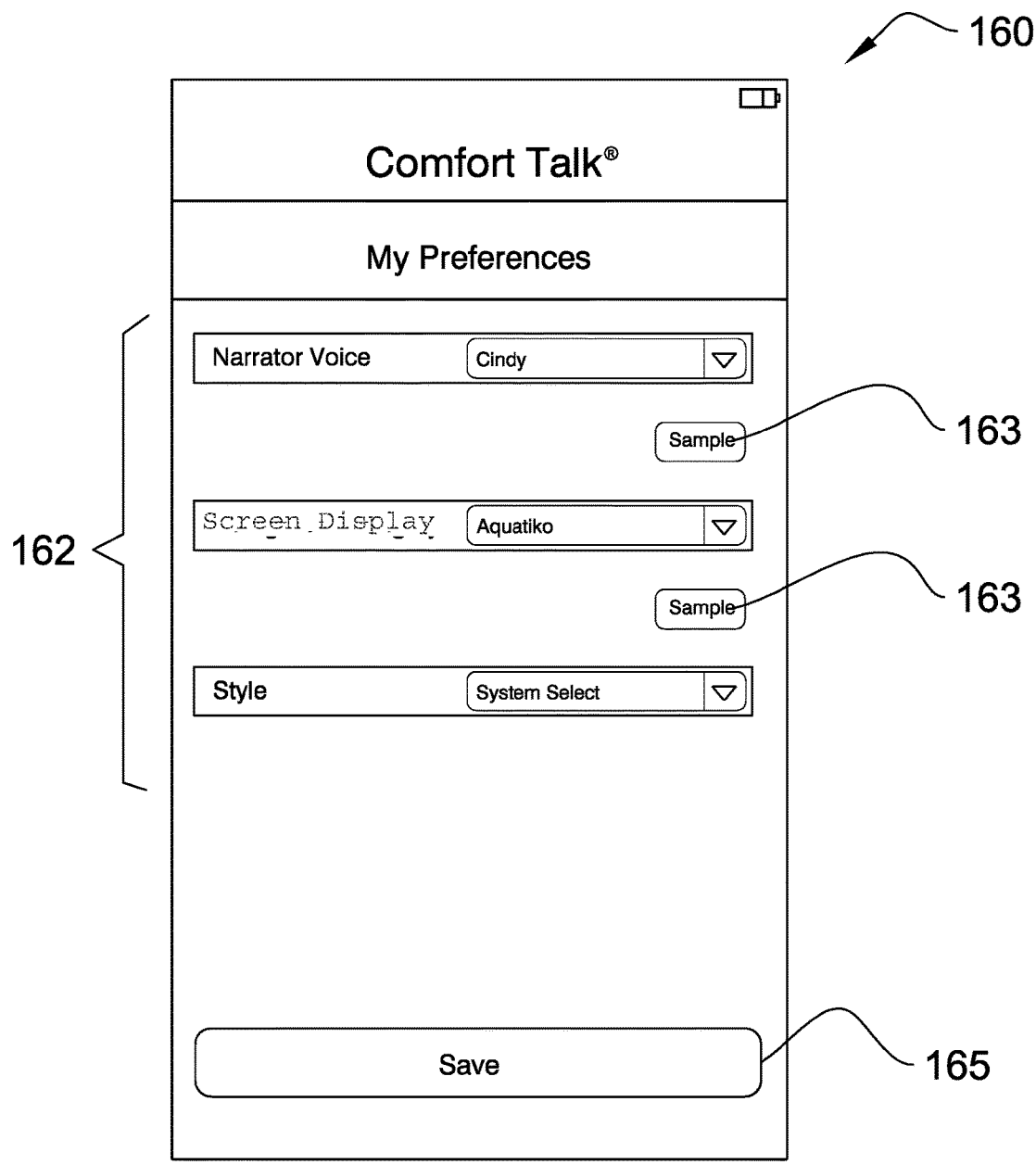
FIG. 6 depicts a preferences screen of the self sedation and suggestion system application, according to certain embodiments.

From the sign in screen, the flow of FIG. 4 moves to Step 12 where a user opts to create a new, customized script. The user already having logged in, application 300 checks to see whether the user has any pre-set preferences on file (Step 13). Though a user may diverge from their preferences, these are features of a script that a user typically prefers regardless of the purpose of a particular script, the time the user has available, or other aspects that may vary more frequently. If preferences exist, flow moves to Step 20 and the preferences are adopted automatically. If they do not exist, the user is prompted to enter them at Step 14. This may launch a new screen, such as preferences screen 160 shown in FIG. 6. Here, preferences are entered via, for example, drop down option boxes 162 for script characteristics such as narrator voice, screen display and style. In some cases, a sample button 163 will be provided for users to help select their preferences. For example, several voices may be pre-loaded in the system application 300 and given names such as Cindy, Joanne, or Robert. Each might use a different pitch, accent, or even volume. A user may want no screen display at all, in which case they would select <none> as an option. However, they may want some type of calming visual effect to assist with them reaching the desired state of focused attention. Such visual effects can also be sampled, in which case the screen will temporarily change and then revert to the preference selection.

In the case of style, a user may opt for the system application to select the best style of script presentation, or may select a style from among pre-set options (such as, e.g., <direct formal>). Generally, prior art systems were designed for use by trained therapists who could analyze patient responses and make proper style selections based on those responses. If a system places that responsibility in the hands of the patient, the patient is likely not going to have the training to make the proper selection. Most users will not understand the different style possibilities and which to choose from. For example, a person might believe they like "straight talk" and being told something directly in a strict subject, predicate format. However, that may not be the style description that most conforms to their individual needs and preferences. Because the proper style varies based on several personality characteristics of the user, the present invention offers a style analysis module 171 that helps determine the proper style for delivery of the script. In other words, it removes the need for the user or patient to have professional training or understanding in neurolinguistic customization.

Assuming the user requests the system to select the style, the module 171 launches and produces a series of question and answer screens such as style analysis screen 170. In the embodiment illustrated in FIG. 7, this screen queries a user to rate certain statements that attempt to describe facts or characteristics about the user. The answers to questions of this variety typically do not change for a given user from one situation to another. For purposes of this application, such questions are referred to as situation independent questions. The module 171 may cycle through several such screens, and statements may be presented in a pre-set order, or may be dynamically selected or formed by the module 171 based on responses to prior questions. While FIG. 7 features statements, the style analysis module could also present questions, and could include example presentation snippets. For example, the module might ask a user to rate how favorable a particular snippet is that, when selected, plays back a short segment of a script that describes a scene in a particular manner. In this manner, the module 171 can perform an automatic sensory selection for the user. Based on the responses, the module selects a particular style most appropriate for the user and stores it in the preferences for that user.

Returning to FIG. 4, a user may save their preferences on preferences screen 160 (Step 16) by selecting button 165 and flow proceeds to Step 20. If they have requested that the system select the style (Step 17), the system first proceeds to style analysis at Step 18, as discussed above, and then stores the result and proceeds to Step 20. Ordinarily, though a user may change preferences, they will not request that the system re-evaluate their style again. Accordingly, the style selection (if system selected) may be assigned a name that the user can recognize and use as a default preference selection. The selected preferences will be used by the system application 300 as inputs in generating a tailored, customized script, as discussed below.

Figure 8:
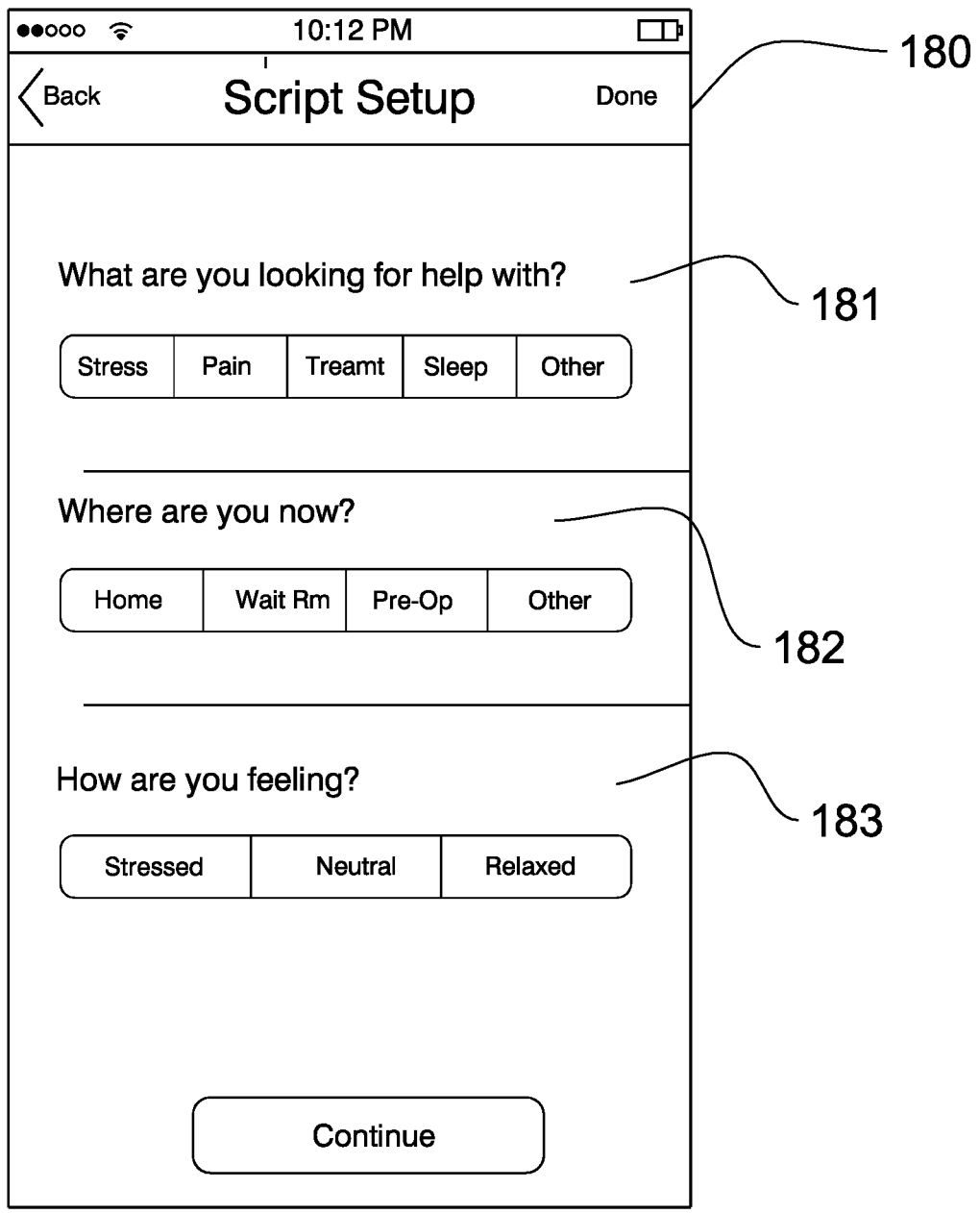
FIG. 8 depicts a first script setup screen of the self sedation and suggestion system application, according to certain embodiments.

At Step 20, the system application 300 gathers information from the user about the script that is to be created. Unlike preference information, the data collected at Step 20 is likely to vary even for a particular user from one use to the next. A sample script setup screen 180 such as might be used in association with step 20 is shown in FIG. 8. The questions 181, 182 and 183 shown in FIG. 8 are unique to the user's particular situation at that time (or at some future time and place where the user expects to be using the script being generated). It will be understood that these are merely exemplary questions, and that others relating to a unique situation could be used. These may be referred to as situation dependent questions. By answering these questions, the user provides additional inputs used by the system application to generate the personalized script. For example, say a user wants to create a script to help them deal with back pain prior to visiting with a prospective client. They are already in the proper mental state, but they want to help remove the pain from their mind to help them focus. This would be the goal they input into the system. Options might be selected such as "Pain," "Wait Rm," and "Relaxed" to help the application build in appropriate messages, tones, music, and other script features.

Figure 9:
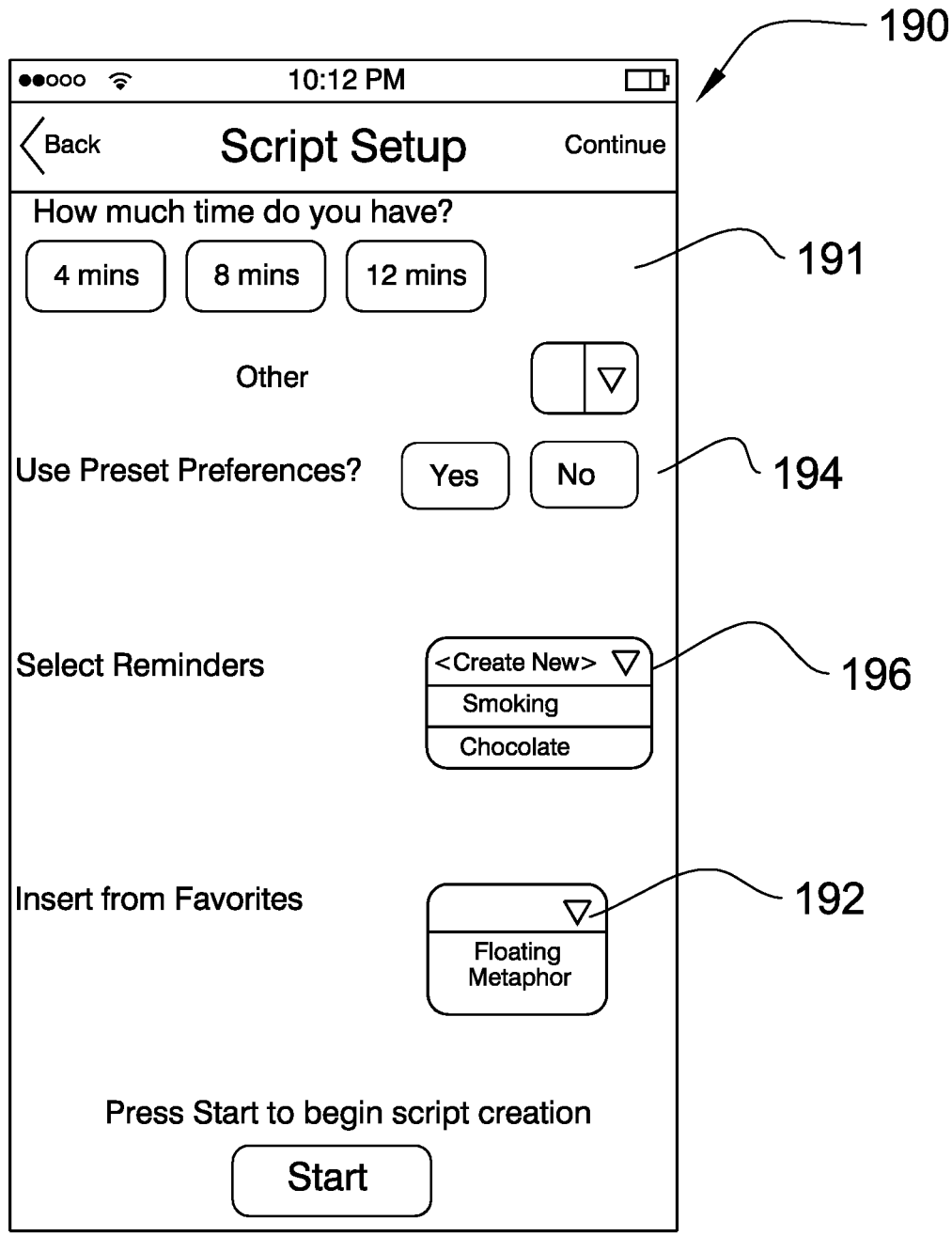
FIG. 9 depicts second script setup screen of the self sedation and suggestion system application, according to certain embodiments.

Next, at Step 22, the user proceeds to script setup screen 190. It will be understood that the setup screens such as screens 180 and 190 may vary and may be broken up into more or less input screens to accomplish the task of gathering the desired input for the application to generate the script. In the illustrated embodiment of FIG. 9, the application asks the user for a desired length of the script at time entry 191. While the length may not be exactly the length of time selected, the application 300 will target this length and choose script components so as to deliver the desired message in a meaningful manner, while allowing for proper introduction and reorientation. For example, the total script playback will be within, say, a minute of the desired length. As those skilled in the art will appreciate, an effective script must generally include an introduction, a message portion, and a reorientation portion. The length and content of the introduction will depend on the experience of the user, and the time available. The general purpose of the introduction is simply to initiate the session, to provide an explanation of what is forthcoming in the script, and to provide directions for entering a proper state to receive the message and later to remove oneself from that state. For example, it might include a simple counting routine, or a more elaborate description of levels of focused attention. The introduction will also include certain triggers to help facilitate reorientation. Once the introduction is complete, the script delivers the message portion of the script, which may include sub-parts, one or more reminders and suggestions towards achieving a desired goal using different types of metaphors, and may be short or long. After the message is effectively delivered, the script concludes with a reorientation portion that helps gently bring the user back to a full state of awareness.

Because a script must generally have these three components, it must be of a certain length to be effective. However, as users become more accustomed to a script, or to use of the sedation and suggestion system generally, they may be able to achieve their goals with a shorter introduction, and to return to full awareness with less reorientation. On the other hand, they may wish to fill longer periods of time remaining in the desired state of focused attention. Accordingly, as described below, the length of a script may be altered by the user even after its initial creation. However, originally, a target length is selected based on factors such as the amount of time a user has available to listen to the script and the receptiveness (and experience) the user has with reaching the desired state of focused attention.

Also at Step 22 and on Screen 190, a user may elect to insert "favorites" from the menu at selection box 192. These "favorites" would be stored in a user profile, and would correspond to specific snippets, or collections of snippets that comprise a message component that the user has identified from a different script in a previous session. A user could select stop and start points in a script (using the interface shown in FIG. 13, for example) to identify a portion as a "favorite" and supply it a name of the user's preference. This "favorite" would then be available through Screen 9 at box 192 for automatic insertion by the system into the new script being developed.

Once the user has entered the desired length of their script and any favorites, Screen 190 gives a user a chance to alter their preferences. Recall that, if preferences were already loaded at Step 13, the user would immediately move to Step 20 (FIG. 4). However, for any number of reasons, the user may, in a particular instance, wish to divert from one or more of their present preferences without permanently changing them. At Step 23 of FIG. 4, the user gets this chance, for example, by selecting "yes" at preference buttons 194 on FIG. 9. If "yes" is selected, the application 300 proceeds to Step 24 (FIG. 4) where changes to the present preferences are taken using a screen similar to that of FIG. 6.

Finally, at Step 25, Screen 190 provides an opportunity for a user to insert reminders at reminder selection box 196. Reminders are components of the message to be delivered in between the introduction and the reorientation. How they are delivered will depend on other inputs, such as, for example, the style. Reminders may be pre-existing or may be user created. They may also be pulled from reminders that the user has created and saved in the past. For example, the reminder "smoking" may comprise a pre-set message that a user has created to help them quit smoking, or may use such a reminder that the system already contained. Thus, the user either selects from a pre-existing reminder at Step 28 or opts to create a new one at Step 26.

Figure 10:
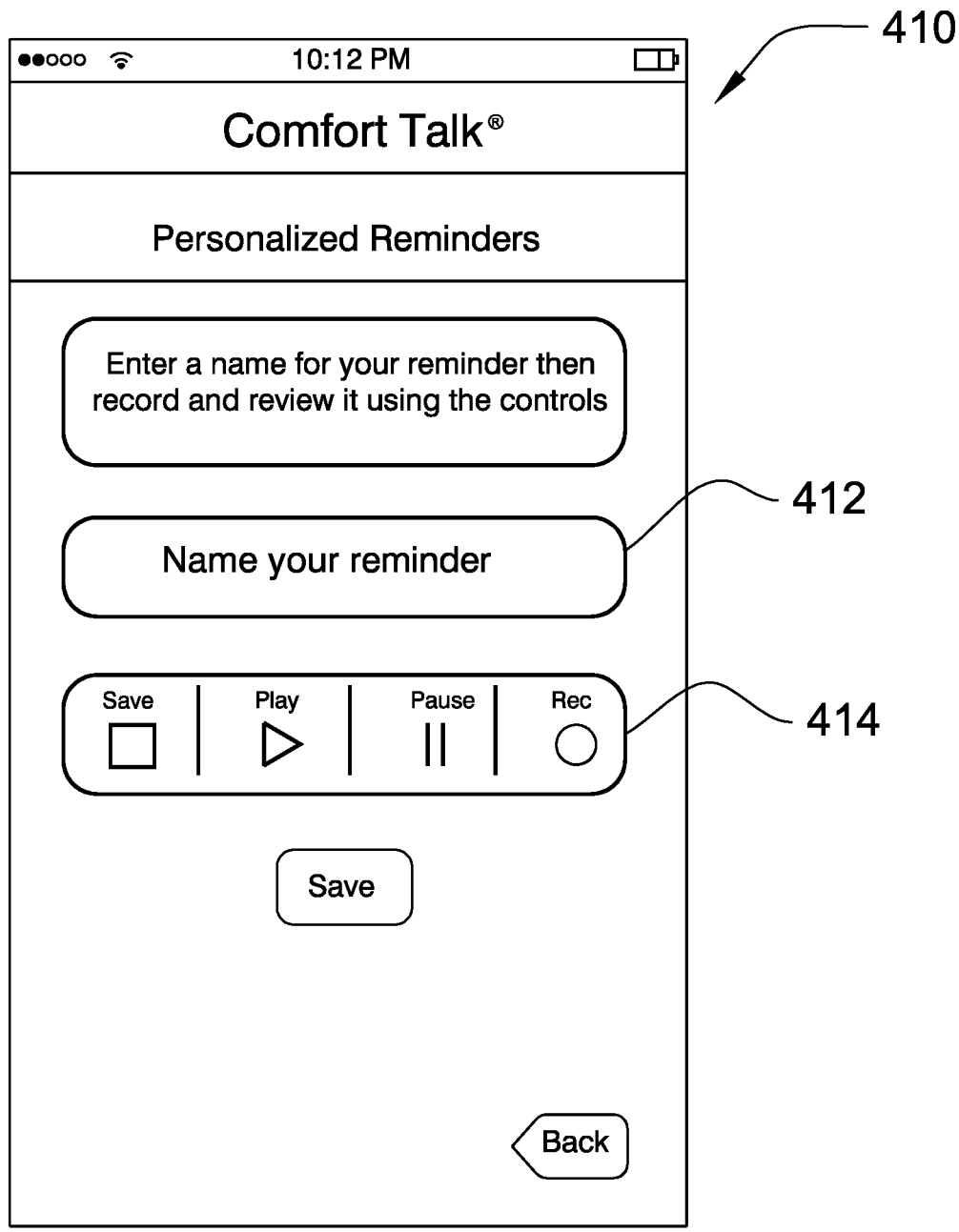
FIG. 10 depicts a reminder recording screen used to record audio for use in a new script of the self sedation and suggestion system application of FIG. 1, according to certain embodiments.

FIG. 10 depicts a reminder creation screen 410 that is used to record new reminders. Here, Application 300 has a record and playback feature that allows a user to speak a new reminder into the mobile device 140 (using, for example, and input/output microphone). The reminder is given a unique name in box 412, and then controls 414 are manipulated to record and play back the reminder. Once the user is happy with the newly recorded reminder, it is saved and will appear as an option in the reminder selection box 196 in future uses. Notably, reminders will be recorded in a user's voice instead of the voice selected in preferences. However, because the reminder is delivered during a state of focused attention, and because a user is typically accustomed to hearing his or her own voice, this is less concerning. However, in some embodiments, Application 300 may utilize a separate module to translate the user's spoken message to text, and then convert the text back into script to be read by the selected voice. In still other embodiments, the user could provide a text string by typing the reminder in to a text box, which could then be converted to a sound file by the Application 300. Allowing for these alternate features requires a large repository of snippet .AVI or other sound files by the recorded voice, and thus, may benefit from a remote call to a server with a larger, centralized storage capability.

At this point in the process of FIG. 4, according to the illustrated embodiment, the Application 300 has all of the inputs required to generate the customized script. Thus, at Step 30, the Application proceeds to generate the script using the inputs. This step uses a script generation engine that compiles a media file of (or approximately of) the desired script length using a variety of snippets (mini-files) stored in, for example, database 314 of FIG. 2 on the mobile device 140. In some cases, the snippets may be many seconds or even several minutes long. For example, typically the beginning part of the message (the initial relaxation instructions) does not vary significantly once certain options are selected. If a user selects a standard theme and a particular voice, for example, there may be little need to vary this component of the script. However, answers to other questions and inputs in setting up the script will call for higher levels of variation where shorter snippets of a few to several seconds or less may be used. For example, a shorter snippet and a longer snippet may both convey the same message component, but one may be selected in lieu of the other so as to comply with the user's requested playback time length. As used herein, "play time" or "playback time" is the amount of time it takes for the file in question to be listened to at its intended pace.

The collection of snippets can be logically organized in the database 314 by the characteristics they are designed to address, such as, for example, pain or anxiety management. They may also be recorded in different ways so as to present according to the proper style for the individual user. Not only does Application 300 select voice/message snippets, background or transition music/sound snippets are also selected and synthesized together (including overlaid so that they play simultaneously) with the voice/message snippets by Application 300 at Step 30 to create the customized script. In addition, user snippets can be inserted into the script by the generation engine where appropriate.

Selected reminders will be inserted within the message portion of the script at effective locations based on programming directives of the Application supplied, for example, by a seasoned therapist. In this manner, critical elements of script formation are not left in the hands of the user, but yet the user has ultimate control over the messaging and the general content. The target time length of the script is also a factor in snippet selection and synthesis by the Application, so as to attain a total script length at or near the target, insuring a proper amount of introduction and reorientation. Any visual component of the script, such as those offered as a sample on FIG. 6 and discussed above, will typically be part of a separate, looping video file that the Application will play on the screen of mobile device 140 concurrently as the audio script file is being played. Thus, there is no need to synthesize audio and video.

Figure 11:
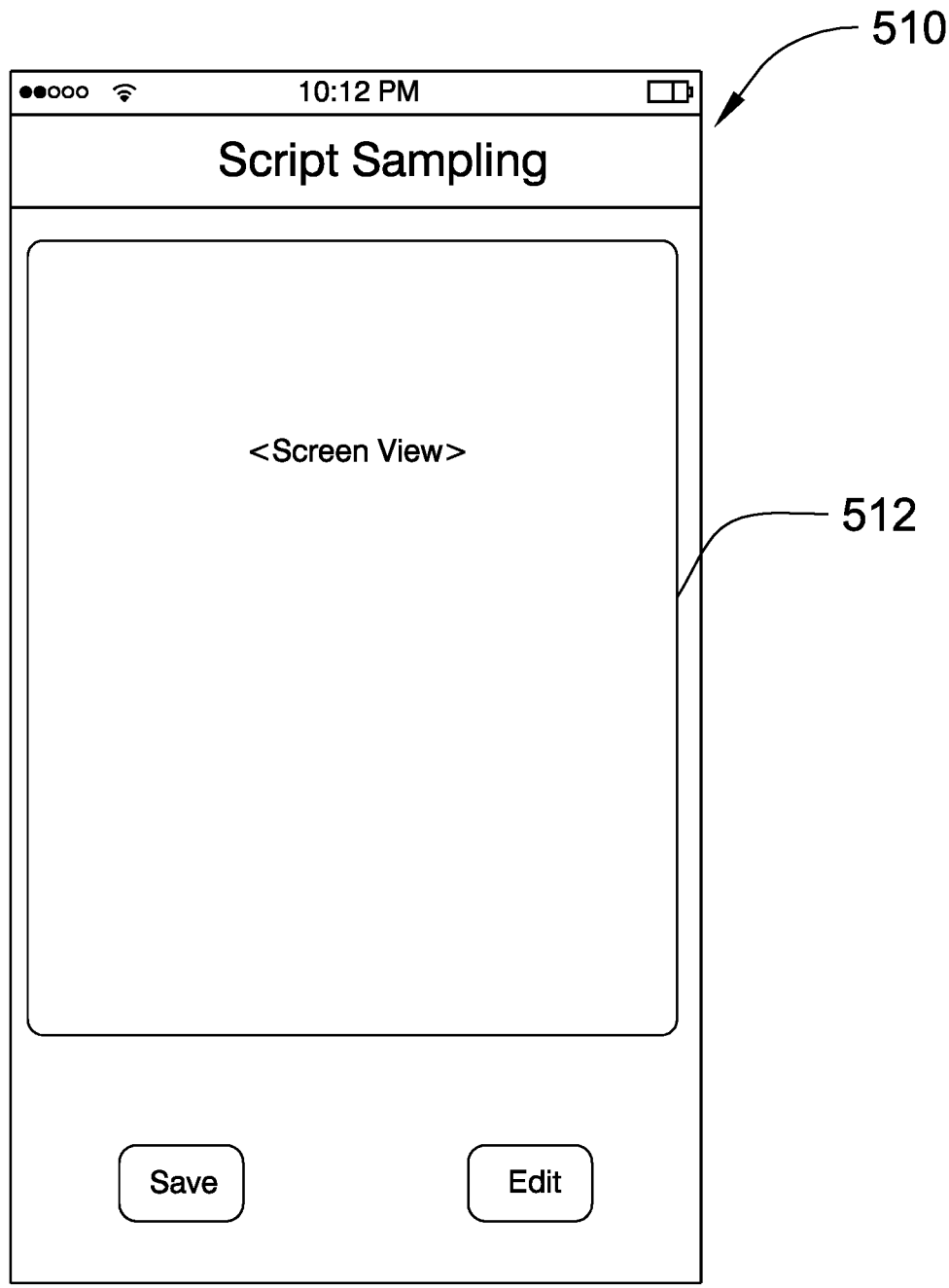
FIG. 11 depicts a script sampling screen for validating new scripts in the self sedation and suggestion system application of FIG. 1, according to certain embodiments.

Once synthesis of the new script is complete, the user samples the script at step 32, modifies it if necessary (such as by returning to one or more of the steps above), and saves it once satisfied. FIG. 11 shows a sampling screen 510 where the script can be sampled, edited, and saved. Again, the screen 512 of FIG. 11 may remain blank during play of the script, or may show a looping video file, depending on the screen display selection. In order to allow a user to form imagery in their mind based on the audio content of the script, most users will listen to scripts with their eyes closed, either from the beginning of playback or from a point somewhere into playback.

Figure 12:
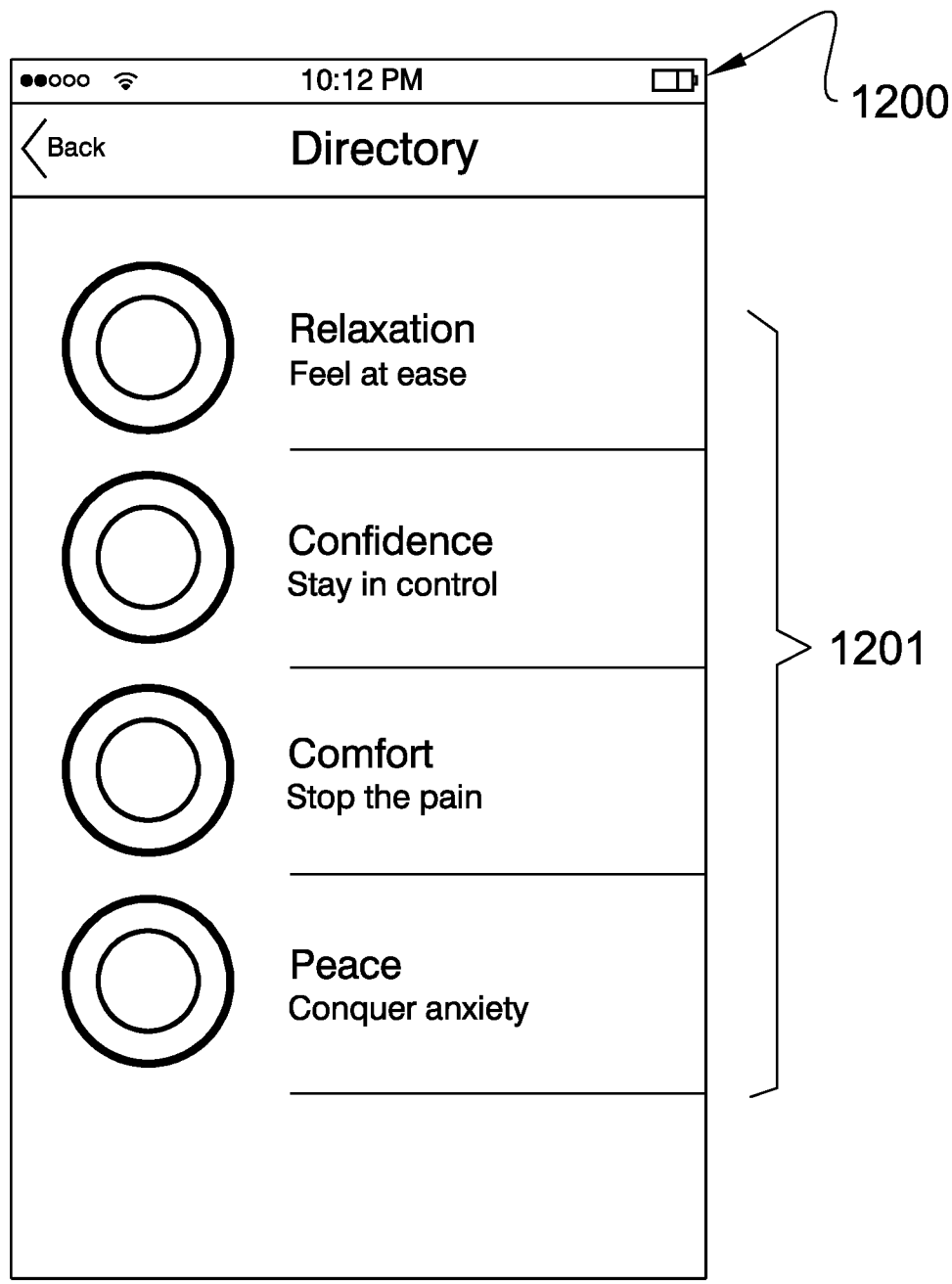
FIG. 12 depicts a script directory interface that allows users to select from among scripts that have been created by the user or the system using the invention described herein.

We have just explored use of the system application 300 to create a new, fully customized script. However, a user may want to simply use a script they have already created, or use a non-customized script that was pre-recorded for a particular issue they are experiencing and is available on database 314 (or on a remote server, available through wireless connection). Turning to FIG. 5, a process flow is shown where a user again starts by logging in to the system at Step 10, but then selects to play a pre-existing script at Step 50. In the illustrated, embodiment, the user is then provided with a topical directory to help narrow down the list of potentially appropriate script files available. An example of such a directory is shown in FIG. 12. Directory screen 1200 has four category options 1201 based on the goal the user seeks to achieve through use of the script. However, it will be understood that there could be more or less options, or the options could be topically divided based on other script characteristics such as, for example, date created, length, reminder content, etc. In other embodiments, the user could simply be provided with an alphabetical list in a file directory format from which they could select a particular script and begin playback.

Figure 13:
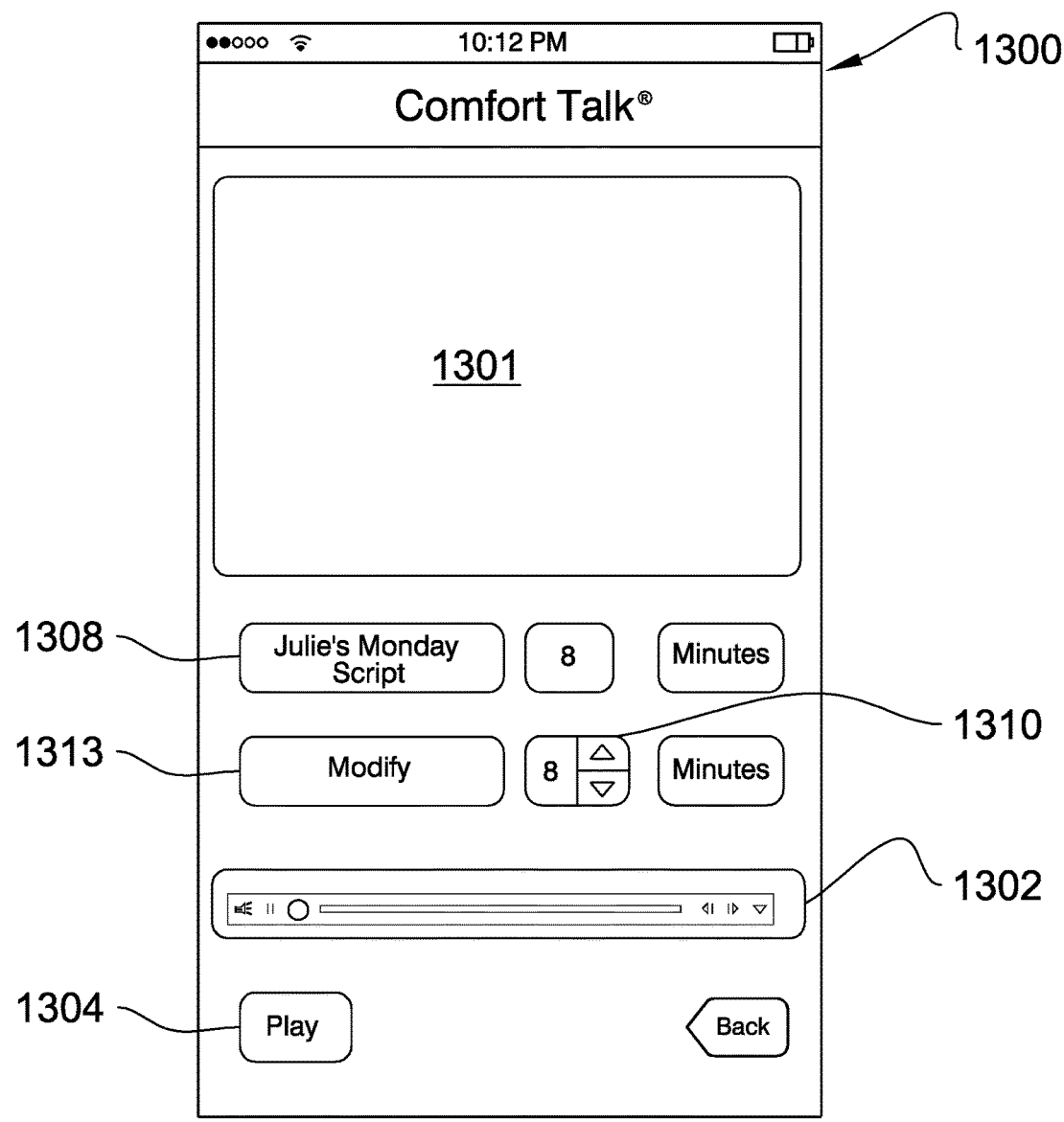
FIG. 13 depicts an interface screen of the application of FIG. 1 showing playback, and offering the user an opportunity to extend or truncate playback from its stored length.

At Step 52, a user negotiates the directory to select a particular script and arrives at a screen such as playback screen 1300 of FIG. 13. Here, the user has selected a script with the saved name "Julie's Monday Script" appearing in the name field 1308. Playback screen 1300 is similar to the sampling screen of FIG. 11, except that it offers a couple of unique capabilities. First, track bar 1302 is provided at the bottom of the screen. This track bar monitors the progress of the script as it plays back and, though not done in typical playback, allows a user to jump into a script at a certain point, such as, for example, to verify its contents at a time prior to or otherwise when not actually using the script to assist with goal achievement. In the case of actual use by a user that has reached a state of focused attention during use of the script, the track bar allows someone nearby to quickly estimate when the user will return to a full state of awareness. The application 300 may operate to maintain this track bar on screen, overriding any default "screen saver" or "screen hibernate" setting.

Finally, time adjustment module 1310 allows a user to dynamically adjust the set length of a pre-existing or pre-assembled script just prior to playback (Step 53). For example, say a pre-existing script that a user wants to hear is at a recorded length of 8 minutes. As shown in the example of FIG. 13, this length will be displayed when the script is loaded for playback on the playback screen 1300. However, say the user is in a hurry, and wants to play a shortened version of the script. In this case, the user can use time adjustment module 1310 to shorten the length of the script. Alternatively, if the user wishes to experience a longer, slower version of the script, she may lengthen its playback time.

If playback time is altered using time adjustment module 1310, the application 300 dynamically adjusts the script to conform more closely to the desired length at Step 54. In a case where a shorter playback time is desired, this is done by substituting shorter snippets for longer ones, removing or reducing the length of pauses where only relaxing music is played, substituting a shorter introduction or reorientation, etc. However, certain elements of the script must remain in place to effectively and safely deliver the message and any reminders contained therein, so the time adjustment function is limited in its ability to shorten a script. For example, an 8 minutes pre-recorded script may be able to be dynamically modified to, say 6 minutes. But not to 2 minutes. In the case where a user wishes to extend playback, application 300 performs opposite types of script modification, such as, for example, adding new or longer "music pauses" or "reflection pauses" in where only relaxing music or relaxing word syllables are played, using a longer, slower introduction or reorientation snippet, etc. Though the edited length can be saved as a new script, the original pre-recorded script is unaffected by the dynamic modification of its length and playback of the modified version. Once the user has made any adjustments desired, the script is played by pressing play 1304 at step 56.

In some embodiments there may be a "Reorient" button available on the screen during playback. Because of the application 300's capability for dynamic modification of the script, the reorient button can be selected by a third party monitoring the user, such as in a case where it is required that the user return to a state of alertness quickly. In this manner, instead of simply interrupting playback abruptly, the third party can allow the Application to alter the playback during use so as to quickly move (skip) to a short but safe and practical reorientation snippet. In this case, reminders and the message may be truncated or not fully delivered, but the user will exit the script in a more fully aware and prepared state than if simply interrupted.

As a user spends more time operating the self sedation and suggestion system, the application 300 will become more accustomed to the user's preferences that may not be directly collected at preferences screen 160. Information about the user may be determined inductively by such things as the user's age, sex or other demographics, the type of mobile device 140 or other computer the person uses to operate the application 300, etc. This material may be stored in database 314 as customer profile information. In addition, the application 300 may provide an option for the user to "like" or "dislike" certain scripts or snippets that the user comes across during operation of script setup so as to help recommend material that will be more favorable to the user. This data may also be stored in association with the customer profile.

While it has been shown how to generate a new script and how to playback an existing script, it will be understood that the Application 300 also can allow for modifying an existing script through a combination of the above disclosure. For example, a user may start at step 50 and proceed to isolate a particular pre-existing script, but may want to, for whatever reason, change the voice reading the script. In this case, once at playback screen 1300, the user could select the modify 1313 button. This would take the user through screens similar to those of FIGS. 6 and 9, but where the defaults are set to what already exists in the selected script. The user may then alter those pre-set selections (such as, for example, input a new reminder, or change out the introduction) and return to playback using the modified script.

Accordingly, it should now be clear how self sedation and suggestion system application 300 can be used to generate truly customized hypnotic scripts. The application does not simply mechanically include pre-recorded selections based on direct user input. Rather, it selects snippets of pre-recordings that fit an analysis of the user based on indirect questioning and analysis. It can also customize by including preferences set by the user, content and even recordings generated by the user. Any order or process descriptions or input selections in the figures should be understood as representing modules, segments, or portions of code which include one or more executable instructions for implementing specific logical functions or steps in the process, and alternate implementations are included within the scope of the embodiments of the present invention in which functions may be executed out of order from that shown or discussed, including substantially concurrently or in reverse order, depending on the functionality involved, as would be understood by those having ordinary skill in the art.

It should be emphasized that the above-described exemplary embodiments of the present invention, and particularly any "preferred" embodiments, are possible examples of implementations, merely set forth for a clear understanding of the principles of the invention. Many other variations and modifications may be made to the above-described embodiments of the invention without substantially departing from the spirit and principles of the invention. All such modifications are intended to be included herein within the scope of this disclosure and the present invention and protected by the following claims.

What is claimed is:

1. A method of electronically modifying a pre-existing hypnotic script media file for use in self-sedation of a user, comprising the steps of:
  receiving, to a processor through a user interface of a software application resident on a mobile device of the user, a first user input defining a selection of the pre-existing hypnotic script media file, wherein the pre-existing hypnotic script media file is comprised of a plurality of pre-recorded snippets that collectively have a first total play time;
  receiving, to the processor through the user interface, a second user input defining a second total play time different than the first total play time;
  modifying, using the processor, the first total play time of the pre-existing hypnotic script media file to be closer to the second total play time, the modifying including automated selection and insertion into the hypnotic script media file by the software application of at least one snippet not previously included in the plurality of pre-recorded snippets;
  receiving, to the processor through the user interface, a third user input defining selection of a play option associated with the modified hypnotic script media file; and
  initiating, by the processor, playback of the modified hypnotic script media file in response to receiving the third user input.

2. The method of claim 1, wherein the automated selection is based on responses received through the user interface to style analysis questions.

3. The method of claim 2, wherein the responses to the style analysis questions are not direct selections of features desired to be in the hypnotic script media file.

4. The method of claim 1, wherein the pre-existing hypnotic script media file comprises an introduction, a message portion, and a reorientation portion.

5. The method of claim 4, wherein the message portion contains at least one snippet recorded by a user.

6. The method of claim 4, further comprising the step of, during playback of the hypnotic script media file by the processor, receiving a request to rapidly end playback and, in response thereto, transitioning to playback of the reorientation portion.

7. The method of claim 6, wherein the transitioning comprises dynamic modification of the hypnotic media script file.

8. The method of claim 1, wherein at least one of the plurality of snippets comprises a video component such that, when the pre-recorded hypnotic script media file is played by the mobile device, an image is displayed on a display screen of the mobile device.

9. The method of claim 8, further comprising displaying, on a display screen of the mobile device, a plurality of user-selectable options corresponding to pre-existing hypnotic script media files, the first user input corresponding to user selection of one of the displayed options.

10. A self sedation and suggestion system, comprising:
  an input component for receiving inputs from a user, including:
    a first user input defining a selection of a pre-existing hypnotic script media file, wherein the pre-existing hypnotic script media file is comprised of a plurality of pre-recorded snippets that collectively have a first total play time, and a second user input defining a second total play time different than the first total play time;

a processor in connection with the input component and configured to modify the pre-existing hypnotic script media file based on the second user input;

a memory in connection with the processor;

a time-adjustment module stored in the memory and directing the processor to modify the first total play time of the pre-existing hypnotic script media file to be closer to the second total play time by selecting at least one of the plurality of pre-recorded snippets that comprise the pre-existing hypnotic script media file and replacing the selected at least one snippet with a replacement snippet to create a modified hypnotic script media file; and an audio output component for enabling playback of the modified hypnotic script media file in response to receiving a third user input from the input component, the third user input defining selection of a play option associated with the modified hypnotic script media file.

11. The system of claim 10, wherein the replacement snippet is an audio clip submitted by the user.

12. The system of claim 10, further comprising an audio recorder for capturing verbal inputs from a user, and wherein at least one of the plurality of pre-recorded snippets is a recording of a verbal input from the user submitted through the audio recorder.

13. The system of claim 10, wherein the selecting and replacing of the at least one of the plurality of pre-recorded snippets is based, at least in part, on an indirect style analysis wherein the user supplies answers to questions not directly related to the pre-recorded hypnotic script.

14. The system of claim 10, wherein the time-adjustment module modifies the first total play time by replacing at least one of the plurality of pre-recorded snippets with at least one snippet not previously in the plurality of pre-recorded snippets.

15. The system of claim 10, further comprising an output component capable of displaying a plurality of user-selectable options representing pre-existing hypnotic script media files, the first user input corresponding to user selection of one of the displayed options.

16. The system of claim 10, further comprising a reorientation module that dynamically modifies the length of the audio script during playback.

17. The system of claim 16, wherein the audio script comprises an introduction portion, a message portion, and a reorientation portion, the system further comprising a reorientation module that shortens the playback time by removing snippets from the message portion during playback.

* * * * *